United States Patent
Ogawa et al.

(10) Patent No.: US 9,539,229 B2
(45) Date of Patent: Jan. 10, 2017

(54) INTESTINAL TRACT-PROTECTING AGENT CONTAINING HYDROXYLATED FATTY ACID

(71) Applicants: KYOTO UNIVERSITY, Kyoto-shi, Kyoto (JP); NITTO PHARMACEUTICAL INDUSTRIES, LTD., Muko-shi, Kyoto (JP)

(72) Inventors: Jun Ogawa, Kyoto (JP); Shigenobu Kishino, Kyoto (JP); Yasunori Yonejima, Muko (JP)

(73) Assignees: Kyoto University, Kyoto (JP); Nitto Pharmaceutical Industries, Ltd., Muko (JP)

(*) Notice: Subject to any disclaimer, the term of this patent is extended or adjusted under 35 U.S.C. 154(b) by 0 days.

(21) Appl. No.: 14/768,183

(22) PCT Filed: Feb. 13, 2014

(86) PCT No.: PCT/JP2014/053383
§ 371 (c)(1),
(2) Date: Aug. 14, 2015

(87) PCT Pub. No.: WO2014/129384
PCT Pub. Date: Aug. 28, 2014

(65) Prior Publication Data
US 2016/0000739 A1    Jan. 7, 2016

(30) Foreign Application Priority Data
Feb. 21, 2013  (JP) ................. 2013-031769

(51) Int. Cl.
C07C 57/00  (2006.01)
A61K 31/201  (2006.01)
C07C 59/42  (2006.01)

(52) U.S. Cl.
CPC .......... *A61K 31/201* (2013.01); *A23K 20/158* (2016.05); *A23L 33/12* (2016.08); *C07C 59/42* (2013.01); *A23V 2002/00* (2013.01)

(58) Field of Classification Search
CPC ..... A61K 31/201; A23K 20/158; A23L 33/12; C07C 59/42
(Continued)

(56) References Cited

U.S. PATENT DOCUMENTS

2005/0032892 A1    2/2005  Kelm et al.

FOREIGN PATENT DOCUMENTS

| IT | WO 9916435 A1 * | 4/1999 | ............. A61K 31/20 |
| JP | 09-241177 A | 9/1997 | |

(Continued)

OTHER PUBLICATIONS

Japanese Patent Office, International Search Report in International Patent Application No. PCT/JP2014/053383 (May 20, 20104).
(Continued)

*Primary Examiner* — Deborah D Carr
(74) *Attorney, Agent, or Firm* — Leydig, Voit & Mayer, Ltd.

(57) ABSTRACT

The present invention provides an intestinal tract-protecting agent, an agent for the prophylaxis or improvement of a disease caused by damage in intestinal tract barrier function, which contains hydroxylated fatty acid, particularly hydroxylated unsaturated fatty acid, having a hydroxyl group at the 10-position and/or the 12-position, which is an intermediate of the metabolism of unsaturated fatty acid by *lactobacillus*.

8 Claims, 8 Drawing Sheets

(58) Field of Classification Search
USPC .......................................................... 554/230
See application file for complete search history.

(56) References Cited

FOREIGN PATENT DOCUMENTS

| JP | 2003-073286 A | 3/2003 | |
| KR | WO 2010117194 A2 * | 10/2010 | ............. A61K 31/20 |
| WO | WO 99/16435 A1 | 4/1999 | |
| WO | WO 2010/117194 A2 | 10/2010 | |

OTHER PUBLICATIONS

Ha et al., *Carcinogenesis*, 8(12): 1881-1887 (1987).
Ip et al., *Cancer Research*, 51: 6118-6124 (1991).
Lee et al., *Atherosclerosis*, 108: 19-25 (1994).
Nusrat et al., *Am. J. Physiol. Gastrointest. Liver Physiol.*, 279: G851-G857 (2000).
Kametani et al., *Bioscience, Biotechnology, and Biochemistry*, 71(5): 1220-1229 (2007).
European Patent Office, Extended European Search Report in European Patent Application No. 14754333.4 (Jul. 26, 2016).

* cited by examiner

A : Hydroxyl Fatty Acids

HYA : 10-hydroxy-12(Z)-18:1

HYB : 10-hydroxy-18:0

B : Ketone Fatty Acids

Keto A : 10-oxo-12(Z)-18:1

Keto B : 10-oxo-18:0

Keto C : 10-oxo-11(E)-18:1

A

B

INTESTINAL TRACT-PROTECTING AGENT CONTAINING HYDROXYLATED FATTY ACID

CROSS-REFERENCE TO RELATED APPLICATIONS

This patent application is the U.S. national phase of International Patent Application No. PCT/JP2014/053383, filed Feb. 13, 2014, which claims the benefit of Japanese Patent Application No. 2013/031769, filed on Feb. 21, 2013, which are incorporated by reference in their entireties herein.

INCORPORATION-BY-REFERENCE OF MATERIAL ELECTRONICALLY SUBMITTED

Incorporated by reference in its entirety herein is a computer-readable nucleotide/amino acid sequence listing submitted concurrently herewith and identified as follows: 8,306 bytes ASCII (Text) file named "721625SequenceListing.txt," created Aug. 14, 2015.

TECHNICAL FIELD

The present invention relates to an intestinal tract-protecting agent containing a hydroxylated fatty acid. Particularly, the present invention relates to an intestinal tract-protecting agent containing a hydroxylated unsaturated fatty acid. More particularly, it relates to the improvement of an intestinal tract barrier function by 10-hydroxy-cis-12-octadecenoic acid and the like.

BACKGROUND ART

Intestine epithelial cells are in direct contact with foods, enteric bacteria, pathogens and the like. They do not simply function as a physical barrier, but also play an important role in the induction of and giving direction to immune responses in the intestine, and the like. Intestine epithelial cells form a structure wherein intercellular spaces are closely adhered by plural tight junction-related factors such as ZO-1, Occludin and Claudin firmly. When the expression of said related factors decreases and the like in the intestinal epithelial cells due to IL-6, TNF-α, insulin and the like, the intestinal tract barrier function may sometimes be damaged (non-patent document 1). Also, when the intestinal epithelial cell layer is damaged by pathogen and the like, peripheral immunocytes are activated to repair the epithelial layer and remove foreign substances.

However, when immune response becomes excessive, inflammation may occur in the intestinal tissues and, as a therapeutic agent to suppress such inflammation, a therapeutic agent for inflammatory bowel diseases, which contains *lactobacillus* bacterium, and the like have been reported (patent document 1). As a therapeutic drug that suppresses permeation of allergen substances and the like by taking note of substance permeation through tight junction and preventing looseness of the tight junction, intestinal tract-protecting agents containing whey protein, casein, serum albumin and the like as an active ingredient and the like have also been reported (patent document 2).

While the above-mentioned intestinal tract-protecting agents have been reported, the development of a new intestinal tract-protecting agent, which can be used for the prophylaxis or treatment of damage in intestinal tract barrier function or diseases caused thereby is desired.

Conjugated fatty acid represented by conjugated linoleic acid (CLA) has been reported to have various physiological activities such as a lipid metabolism improving effect, an anti-arteriosclerosis action, a body fats decreasing action and the like (non-patent documents 2-4), and is a functional lipid expected to be applicable to various fields of medicament, functional food and the like. In addition, action on the intestinal tract protection has been attracting attention and improvement of symptoms of patients with ulcerative colitis such as Crohn's disease and the like, by conjugated linoleic acid has been reported and the like (http://www.nimml.org/838/).

Conjugated linoleic acid is produced as an intermediate of saturation metabolism of unsaturated fatty acid by *lactobacillus*. As an intermediate of the metabolism, for example, hydroxylated fatty acids such as 10-hydroxy-cis-12-octadecenoic acid, 10-hydroxy-octadecanoic acid and the like, oxofatty acids such as 10-oxo-12-octadecenoic acid, 10-oxooctadecanoic acid, 10-oxo-11-octadecenoic acid and the like, and the like exist. However, there is no report on the action and effect of an intermediate of saturation metabolism of unsaturated fatty acid by *lactobacillus* on the intestine, as far as the applicant is aware of.

DOCUMENT LIST

Patent Documents patent document 1: JP-A-2003-073286
patent document 2: JP-A-9-241177

Non-Patent Documents non-patent document 1: Nusrat A, (2000), Am J Physiol Gastrointest Liver Physiol., vol. 279, no. 5, p. G851-G857
non-patent document 2: Ha Y L, (1987), Carcinogenesis, vol. 8, no. 12 p. 1881-1887
non-patent document 3: Clement Ip, (1991), Cancer Res., (1991), vol. 51, p. 6118-6124
non-patent document 4: Kisun N L, (1994), Atherosclerosis, vol. 108, p. 19-25

SUMMARY OF THE INVENTION

Problems to be Solved by the Invention

An object of the present invention is to provide a novel intestinal tract-protecting drug, which can be used for the prophylaxis or treatment of damage in the intestinal tract barrier function or diseases caused thereby.

Means of Solving the Problems

The present inventors have conducted intensive studies in view of the above-mentioned problem and found that hydroxylated fatty acid, particularly hydroxylated unsaturated fatty acid, having 18 carbon atoms and having a hydroxyl group at the 10-position and/or the 12-position, such as 10-hydroxy-cis-12-octadecenoic acid and the like, which is an intermediate of the metabolism of unsaturated fatty acid by *lactobacillus*, has an intestinal tract barrier protecting action, a suppressive action on the expression of inflammatory cytokine IL-8, and a pathology reducing action in enteritis model.

Accordingly, the present invention is as follows.

[1] An intestinal tract-protecting agent comprising a hydroxylated fatty acid having 18 carbon atoms and having a hydroxyl group at the 10- and/or 12-position(s).
[2] The agent of [1], wherein the hydroxylated fatty acid is a hydroxylated unsaturated fatty acid.
[3] The agent of [2], wherein the hydroxylated unsaturated fatty acid has a cis double bond at the 12-position.
[4] The agent of [2], wherein the hydroxylated unsaturated fatty acid is 10-hydroxy-cis-12-octadecenoic acid.
[5] The agent of any of [1]-[4], which is used for the prophylaxis or improvement of a disease caused by damage in intestinal tract barrier function.
[6] The agent of [5], wherein the disease caused by damage in intestinal tract barrier function is at least one kind of disease selected from the group consisting of inflammatory bowel disease, ulcer and irritable bowel syndrome.
[7] The agent of any of [1]-[6], which is a food or a food additive.
[8] The agent of any of [1]-[6], which is a pharmaceutical product.
[9] The agent of any of [1]-[6], which is a feed or a feed additive.
[10] A method for the prophylaxis or treatment of damage in intestinal tract barrier function or a disease caused by the damage in warm-blooded animals, comprising administering an effective amount of a hydroxylated fatty acid having 18 carbon atoms and having a hydroxyl group at the 10- and/or 12-position(s) to a mammal.
[11] A hydroxylated fatty acid having 18 carbon atoms and having a hydroxyl group at the 10- and/or 12-position(s), which is for use as an intestinal tract-protecting agent.
[12] Use of a hydroxylated fatty acid having 18 carbon atoms and having a hydroxyl group at the 10- and/or 12-position(s), for the production of an intestinal tract-protecting agent.

Effect of the Invention

In the present invention, it has been clarified that hydroxylated fatty acid, particularly hydroxylated unsaturated fatty acid, having 18 carbon atoms and having a hydroxyl group at the 10-position and/or the 12-position, such as 10-hydroxy-cis-12-octadecenoic acid (hereinafter to be also referred to as HYA) has an intestinal tract barrier protecting action which is not conventionally known. The present invention can provide, based on such action, an intestinal tract-protecting agent containing the fatty acid. Since the agent can be used in various fields such as pharmaceutical product, food, feed and the like, the present invention is industrially extremely useful.

BRIEF DESCRIPTION OF THE DRAWINGS

FIG. 2B shows relative values of TER value when the value of the control (None) group at 6 hr of culture in FIG. 2A is 1. In the Figure, * vs None, # vs (-), $ vs HYA are shown, two marks show P<0.01, and one mark shows P<0.05 (the same also in FIGS. 3-8 and 10).

DESCRIPTION OF EMBODIMENTS

Figure 1:
FIG. 1 shows the structural formulas of fatty acids used in Examples.
Figure 1:
Figure 1:
Figure 1:
Figure 1:

The present invention is explained in detail below. The present invention provides an intestinal tract-protecting agent containing hydroxylated fatty acid having 18 carbon atoms and having a hydroxyl group at the 10-position and/or the 12-position, such as 10-hydroxy-cis-12-octadecenoic acid (hereinafter to be also referred to as "hydroxylated fatty acid of the present invention").

In the present invention, "the intestinal tract protection" means repair of damaged intestinal tract barrier function and/or enhancement of intestinal tract barrier function. As for damage, the extent thereof is not significant and it includes any of a severe level to a light level. Repair of the function means bringing an abnormal state to the original state and/or a state close to the original state. Enhancement of function includes enforcing the function and, in some cases, suppressing a decrease in the function as well.

In the present invention, "the intestinal tract barrier (function)" physically means prevention of permeation of a substance other than low molecules by forming a structure wherein intercellular spaces between intestinal epithelial cells are strongly and closely adhered by tight junction-related factors. Biologically, it means extracorporeal discharge of foreign substances via a transporter and the like present in the intestinal epithelial cells, or intestinal mucosal defense by IgA secreted in the intestinal mucosa upon antigen stimulation.

In the present invention, the intestinal tract barrier function can be evaluated by a method known per se. For example, changes in feces, changes in body weight and the like when the hydroxylated fatty acid of the present invention is administered to T cell-transferred enteritis animal (animal models of Crohn's disease and the like) can be confirmed. Alternatively, as described in the below-mentioned Examples, human gastrointestinal tract epithelial cell line Caco-2 cells widely used as small intestine epithelial model may be externally stimulated by cytokines such as TNF-α and/or IFN-γ to damage the cells, the hydroxylated fatty acid of the present invention is administered, and transepithelial electrical resistance (TER) value, expression level of cytokine such as IL-8, or expression level of tight junction-related factor is measured, and the like. However, these methods are not limitative. The tight junction-related factors also include known and/or unknown factors, such as ZO-1, Occludin, Claudin, MLCK (myosin light chain kinase) and the like. The expression level of the factor can be measured by a method known per se such as real-time PCR, ELISA method and the like.

In the present invention, the "prophylaxis or improvement of damage in intestinal tract barrier function" which provides "the intestinal tract protecting" effect means that the evaluation of the intestinal tract barrier function by at least any one of the above-mentioned methods is significantly improved by the administration of test hydroxylated fatty acid.

"The hydroxylated fatty acid of the present invention" refers to a hydroxylated fatty acid having 18 carbon atoms and a hydroxyl group at the 10-position (hereinafter sometimes to be abbreviated as "10-hydroxylated fatty acid"), or a hydroxylated fatty acid having 18 carbon atoms and a hydroxyl group at the 12-position (hereinafter sometimes to be abbreviated as "12-hydroxylated fatty acid"). Here, a "10,12-dihydroxylated fatty acid" having a hydroxyl group at the 10- and 12-positions is also encompassed as one embodiment of "10-hydroxylated fatty acid", "12-hydroxylated fatty acid". Furthermore, a hydroxylated fatty acid having 18 carbon atoms, a hydroxy group at the 10-position and a cis double bond at the 12-position (hereinafter sometimes to be abbreviated as "10-hydroxy,cis-12 fatty acid"), a hydroxylated fatty acid having 18 carbon atoms, a hydroxyl group at the 10-position and a trans double bond at the 11-position (hereinafter sometimes to be abbreviated as "10-hydroxy,trans-11 fatty acid"), and a hydroxylated fatty acid having 18 carbon atoms and a hydroxyl group at the 10-position and free of a double bond at the 11 and 12-positions (hereinafter sometimes to be abbreviated as "10-hydroxy,11,12-saturated fatty acid") are also encompassed.

More specific examples include, but are not limited to, 10-hydroxy-cis-12-octadecenoic acid (HYA), 10-hydroxy-cis-12,cis-15-octadecadienoic acid (hereinafter to be also referred to as "αHYA"), 10-hydroxy-cis-6,cis-12-octadecadienoic acid (hereinafter to be also referred to as "γHYA"), 10-hydroxy-cis-6,cis-12,cis-15-octadecatrienoic acid (hereinafter to be also referred to as "sHYA"), 10,12-dihydroxyoctadecanoic acid (hereinafter to be also referred to as "rHYA"), 10-hydroxyoctadecanoic acid (hereinafter to be also referred to as "HYB"), 10-hydroxy-cis-15-octadecenoic acid (hereinafter to be also referred to as "αHYB"), 10-hydroxy-cis-6-octadecenoic acid (hereinafter to be also referred to as "γHYB"), 10-hydroxy-cis-6,cis-15-octadecadienoic acid (hereinafter to be also referred to as "sHYB"), 12-hydroxyoctadecanoic acid (hereinafter to be also referred to as "rHYB"), ricinoleic acid (hereinafter to be also referred to as "RA"), 10-hydroxy-trans-11-octadecenoic acid (hereinafter to be also referred to as "HYC"), 10-hydroxy-trans-11,cis-15-octadecadienoic acid (hereinafter to be also referred to as "αHYC"), 10-hydroxy-cis-6,trans-11-octadecadienoic acid (hereinafter to be also referred to as "γHYC"), 10-hydroxy-cis-6,trans-11,cis-15-octadecatrienoic acid (hereinafter to be also referred to as "sHYC") and the like.

While the "hydroxylated unsaturated fatty acid of the present invention" is not particularly limited as long as it is the "hydroxylated fatty acid of the present invention" having one or more unsaturated bonds. Preferable examples thereof include those having 1 to 3 double bonds at particular positions (e.g., HYA, αHYA, γHYA, sHYA, αHYB, γHYB, sHYB, RA, HYC, αHYC, γHYC, sHYC etc.). More preferred are those having a cis double bond at the 12-position (e.g., HYA, αHYA, γHYA, sHYA etc.), and particularly preferred is HYA.

A part of fatty acid of the "hydroxylated fatty acid of the present invention" can be obtained using oxo fatty acid as a starting material or intermediate. In the present specification, the oxofatty acid refers to an oxofatty acid having 18 carbon atoms and having a carbonyl group at the 10-position or 12-position (hereinafter sometimes to be abbreviated as "10-oxofatty acid" or "12-oxofatty acid"). Particularly, the above-mentioned 10-hydroxy,trans-11 fatty acid and 10-hydroxy,11,12-saturated fatty acid can be produced by a dehydrogenase reaction (the below-mentioned reactions 5, 6) using an oxo fatty acid having 18 carbon atoms and having a carbonyl group at the 10-position and a trans double bond at the 11-position (hereinafter sometimes to be abbreviated as "10-oxo,trans-11 fatty acid"), and an oxo fatty acid having 18 carbon atoms and having a carbonyl group at the 10-position and free of a double bond at the 11 and 12-positions (hereinafter sometimes to be abbreviated as "10-oxo,11,12-saturated fatty acid"), respectively, as starting materials. The 10-oxo,trans-11 fatty acid can be produced from a hydroxylated fatty acid having 18 carbon atoms and having a carbonyl group at the 10-position and a cis double bond at the 12-position (hereinafter sometimes to be abbreviated as "10-oxo,cis-12 fatty acid") by an isomerase reaction (the below-mentioned reaction 3). The 10-oxo,11,12-saturated fatty acid can be produced from 10-oxo,trans-11 fatty acid by a saturated enzyme reaction (the below-mentioned reaction 4).

More specifically, as the production starting material or intermediate of the hydroxylated fatty acid of the present invention, 10-oxo,cis-12 fatty acids such as 10-oxo-cis-12-octadecenoic acid (also to be referred to as "KetoA"), 10-oxo-cis-12,cis-15-octadecadienoic acid (hereinafter also to be referred to as "αKetoA"), 10-oxo-cis-6,cis-12-octadecadienoic acid (hereinafter also to be referred to as "γKetoA"), 10-oxo-cis-6,cis-12,cis-15-octadecatrienoic acid (hereinafter also to be referred to as "sKetoA") and the like, 10-oxo,11,12-saturated fatty acids such as 10-oxo octadecanoic acid (also to be referred to as "KetoB"), 10-oxo-cis-6-octadecenoic acid (hereinafter also to be referred to as "γKetoB"), 10-oxo-cis-15-octadecenoic acid (hereinafter also to be referred to as "αKetoB"), 10-oxo-cis-6,cis-15-octadecadienoic acid (hereinafter also to be referred to as "sKetoB") and the like, 10-oxo,trans-11 fatty acids such as 10-oxo-trans-11-octadecenoic acid (also to be referred to as "KetoC"), 10-oxo-cis-6,trans-11-octadecadienoic acid (hereinafter also to be referred to as "γKetoC"), 10-oxo-trans-11,cis-15-octadecadienoic acid (hereinafter also to be referred to as "αKetoC"), 10-oxo-cis-6,trans-11,cis-15-octadecatrienoic acid (hereinafter also to be referred to as "sKetoC") and the like, and the like can be used.

The hydroxylated fatty acid of the present invention can be prepared by the method described in Japanese patent application No. 2012-108928, and HYA can be prepared by reference to Biochemical and Biophysical Research Communications 416 (2011) p. 188-193 and the like. As RA, rHYB and the like, commercially available products can be used.
(Reaction 1)

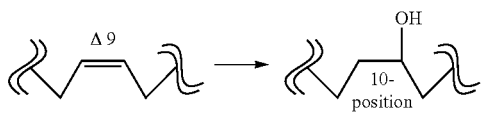

10-oxo fatty acid is produced from an unsaturated fatty acid having 18 carbon atoms and a cis double bond at the 9-position (hereinafter sometimes to be abbreviated as "cis-9 unsaturated fatty acid") by two-step reaction. In the first reaction (reaction 1), 10-hydroxylated fatty acid is produced from cis-9 unsaturated fatty acid by a hydratase reaction.

The substrate in "reaction 1" is not particularly limited as long as it is an unsaturated fatty acid having 18 carbon atoms and a cis double bond at the 9-position, and examples thereof include monoeneoic acid (18:1), dienoic acid (18:2), trienoic acid (18:3), tetraenoic acid (18:4), pentaenoic acid (18:5) and the like. More preferred are dienoic acid, trienoic acid and tetraenoic acid, and particularly preferred are dienoic acids and trienoic acids. In the present specification, "fatty acid" encompasses not only free acids but also ester form, salt with basic compound and the like.

Examples of the monoenoic acid include oleic acid, ricinoleic acid and the like.

Examples of the dienoic acid include linoleic acid, cis-9, trans-11-octadecadienoic acid and the like.

Examples of the trienoic acids include α-linolenic acid, γ-linolenic acid and the like.

Examples of the tetraenoic acid include stearidonic acid and the like.

While hydratase that catalyzes reaction 1 is not particularly limited as long as it is an enzyme capable of utilizing the above-mentioned cis-9 unsaturated fatty acid as a substrate and capable of converting to 10-hydroxylated fatty acid, for example, lactobacillus-derived fatty acid-hydratase (CLA-HY) is preferable. More preferred is Lactobacillus plantarum-derived CLA-HY, and particularly preferred is L. plantarum FERM BP-10549 strain-derived CLA-HY. CLA-HY can be obtained by the method described in JP-A-2007-259712, or the like.

The amount of hydratase to be added is, for example, 0.001-10 mg/ml, preferably 0.1-5 mg/ml, more preferably 0.2-2 mg/ml.

A "cofactor" may be used for reaction 1 and, for example, NADH, NADPH, FADH$_2$ and the like can be used. The concentration of addition may be any as long as the hydration reaction proceeds efficiently. It is preferably 0.001-20 mM, more preferably 0.01-10 mM.

Furthermore, an "activator" may be used for the enzyme reaction and, for example, one or more compounds selected from the group consisting of potassium molybdate, disodium molybdate(VI) anhydrate, disodium molybdate(VI) dihydrate, sodium orthovanadate(V), sodium metavanadate (V), potassium tungstate(VI), sodium tungstate(VI) anhydrate and sodium tungstate(VI) dihydrate can be mentioned. The concentration of addition thereof may be any as long as the hydration reaction proceeds efficiently. It is preferably 0.1-20 mM, more preferably 1-10 mM.

For example, rHYA can be obtained by adding 100 mM potassium phosphate buffer (pH 6.5) containing hydration enzyme (wet bacteria body weight 0.7 g) expressed in Escherichia coli, NADH (33 mg), FAD (0.8 mg), ricinoleic acid (1 g), BSA (0.2 g) to RA to a total amount of 10 ml, and performing a shaking reaction anaerobically at 37° C. for 63 hr, 225 rpm.

On the other hand, 12-hydroxylated fatty acid can be obtained, for example, by hydrolysis of natural oil containing, as a main component, triglyceride ester containing 12-hydroxylated fatty acid as a constituent fatty acid. For example, RA can be obtained by hydrolysis of castor oil, and rHYB can be obtained by hydrolysis of hydrogenated castor oil.
(Reaction 2)

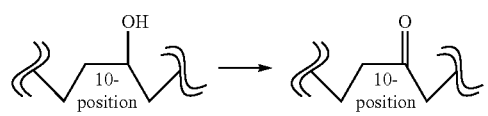

In the second reaction (reaction 2), 10-oxo fatty acid is produced from 10-hydroxylated fatty acid by a dehydrogenase reaction or chemical oxidation using chromic acid.

While the dehydrogenase that catalyzes reaction 2 is not particularly limited as long as it is an enzyme capable of utilizing 10-hydroxylated fatty acid as a substrate and capable of converting to 10-oxo fatty acid, for example, lactobacillus-derived hydroxylated fatty acid-dehydrogenase (CLA-DH) is preferable. More preferred is Lactobacillus plantarum-derived CLA-DH, and particularly preferred is L. plantarum FERM BP-10549 strain-derived CLA-DH. CLA-DH can be obtained by the method described in JP-A-2007-259712, or the like.

The amount of dehydrogenase to be added is, for example, 0.001-10 mg/ml, preferably 0.1-5 mg/ml, more preferably 0.2-2 mg/ml.

A "cofactor" may be used for reaction 2 and, for example, NAD, NADP, FAD and the like can be used. The concentration of addition may be any as long as the oxidation reaction proceeds efficiently. It is preferably 0.001-20 mM, more preferably 0.01-10 mM.

Furthermore, an "activator" may be used for the enzyme reaction and, for example, compounds similar to those recited as examples in the above-mentioned reaction 1 can be used at a similar addition concentration.

The second reaction can be performed by chemical oxidation.

As the chemical oxidation, methods known per se, for example, chromic acid oxidation, preferably Jones oxidation and the like can be mentioned. As the chromic acid, salts and complexes of the compound such as anhydrous chromic acid CrO$_3$, chromic acid H$_2$CrO$_4$ and dichromic acid H$_2$Cr$_2$O$_7$ can be used.
(Reaction 3)

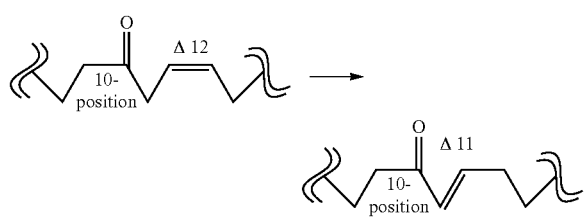

10-Oxo,trans-11 fatty acid is produced from an oxo fatty acid having 18 carbon atoms, a carbonyl group at the 10-position and a cis double bond at the 12-position by an isomerase reaction (reaction 3).

The "substrate" of reaction 3 is not particularly limited as long as it is 10-oxo,cis-12 fatty acid induced from an unsaturated fatty acid having 18 carbon atoms and a cis double bond at the 9- and 12-positions, by the above-mentioned reactions 1 and 2. Examples thereof include KetoA induced from linoleic acid, αKetoA induced from α-linolenic acid, γKetoA induced from γ-linolenic acid, sKetoA induced from stearidonic acid and the like. The substrate may be obtained by a method other than reactions 1 and 2.

While isomerase that catalyzes reaction 3 is not particularly limited as long as it is an enzyme capable of utilizing the above-mentioned 10-oxo,cis-12 fatty acid as a substrate and capable of converting to 10-oxo,trans-11 fatty acid, for example, *lactobacillus*-derived oxo fatty acid-isomerase (CLA-DC) is preferable. More preferred is *Lactobacillus plantarum*-derived CLA-DC, and particularly preferred is *L. plantarum* FERM BP-10549 strain-derived CLA-DC. CLA-DC can be obtained by the method described in JP-A-2007-259712, or the like.

The amount of isomerase to be added is, for example, 0.001-10 mg/ml, preferably 0.1-5 mg/ml, more preferably 0.2-2 mg/ml.

An "activator" may be used for the isomerase reaction and, for example, compounds similar to those recited as examples in the above-mentioned reaction 1 can be used at a similar addition concentration.

(Reaction 4)

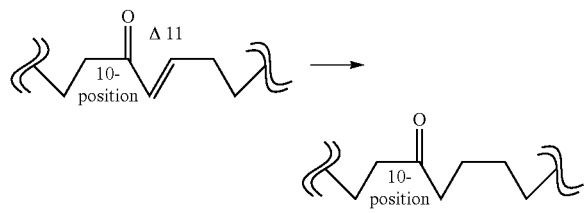

10-Oxo,11,12-saturated fatty acid is produced from an oxo fatty acid having 18 carbon atoms, a carbonyl group at the 10-position and a trans double bond at the 11-position (10-oxo,trans-11 fatty acid) by a saturase reaction (reaction 4).

The "substrate" of reaction 4 is not particularly limited as long as it is 10-oxo,trans-11 fatty acid produced by the above-mentioned reaction 3. Examples thereof include KetoC induced from KetoA, αKetoC induced from αKetoA, γKetoC induced from γKetoA, sKetoC induced from sKetoA and the like. The substrate may be obtained by a method other than reaction 3.

While saturase that catalyzes reaction 4 is not particularly limited as long as it is an enzyme capable of utilizing the above-mentioned 10-oxo,trans-11 fatty acid as a substrate and capable of converting to 10-oxo,11,12-saturated fatty acid, for example, oxo fatty acid-enone reductase (CLA-ER) derived from *lactobacillus* is preferable. More preferred is *Lactobacillus plantarum*-derived CLA-ER, and particularly preferred is *L. plantarum* FERM BP-10549 strain-derived CLA-ER.

The above-mentioned enzyme "CLA-ER" is
(a) an enzyme protein consisting of the amino acid sequence shown in SEQ ID NO: 2,
(b) a protein comprising an amino acid sequence which is the amino acid sequence shown in SEQ ID NO: 2 wherein one or plural amino acids are deleted and/or substituted and/or inserted and/or added, and having an enzyme activity of catalyzing the above-mentioned reaction 4, or
(c) a protein encoded by a base sequence that hybridizes to a nucleic acid consisting of a complementary chain sequence of the base sequence shown in SEQ ID NO: 1 under stringent conditions, and having an enzyme activity to catalyze the above-mentioned reaction 4.

More specific examples of the above-mentioned (b) include a protein containing (i) an amino acid sequence which is the amino acid sequence shown in SEQ ID NO: 2, wherein 1-20, preferably 1-10, more preferably 1-several (5, 4, 3 or 2) amino acids are deleted, (ii) an amino acid sequence which is the amino acid sequence shown in SEQ ID NO: 2, wherein 1-20, preferably 1-10, more preferably 1-several number (5, 4, 3 or 2) amino acids are added, (iii) an amino acid sequence which is the amino acid sequence shown in SEQ ID NO: 2, wherein 1-20, preferably 1-10, more preferably 1-several (5, 4, 3 or 2) amino acids are inserted, (iv) an amino acid sequence which is the amino acid sequence shown in SEQ ID NO: 2, wherein 1-20, preferably 1-10, more preferably 1-several (5, 4, 3 or 2) amino acids are substituted by other amino acids, or (v) an amino acid sequence obtained by combining them. When amino acids with similar properties (e.g., glycine and alanine, valine and leucine and isoleucine, serine and threonine, aspartic acid and glutamic acid, asparagine and glutamine, lysine and arginine, cysteine and methionine, phenylalanine and tyrosine etc.) are substituted with each other and the like, a greater number of substitutions and the like are possible.

When amino acids are deleted, substituted or inserted as mentioned above, the positions of deletion, substitution and insertion are not particularly limited as long as the above-mentioned enzyme activity is maintained.

In the above-mentioned (c), the "stringent conditions" are conditions under which nucleotide sequences having high identity, for example, identity of 70, 80, 90, 95 or 99% or above, hybridize to each other and nucleotide sequences having identity lower than that do not hybridize; specifically, conditions of washing once, more preferably 2-3 times, at the salt concentration and temperature corresponding to those in the washing conditions of general Southern hybridization (60° C., 1×SSC, 0.1% SDS, preferably, 0.1×SSC, 0.1% SDS, more preferably, 68° C., 0.1×SSC, 0.1% SDS) and the like.

CLA-ER can be isolated from, for example, the fungus and culture medium of *L. plantarum* FERM BP-10549 strain, for example, by using the enzyme activity that catalyzes the above-mentioned reaction 4 as an index. Alternatively, it can also be produced by recombination by synthesizing the total base sequence of the coding region of CLA-ER based on the information of the base sequence shown in SEQ ID NO: 1, or designing a primer capable of amplifying CLA-ER gene segment containing the coding region, performing PCR using cDNA or genome DNA prepared from the above-mentioned strain as a template, cloning the obtained amplification fragment to a suitable expression vector and introducing same into a host cell, and cultivating the cell.

As a vector containing a nucleic acid encoding the above-mentioned CLA-ER, one suitable for a host cell to be introduced with the vector may be appropriately selected according to the object (e.g., protein expression) and can be used. The expression vector can contain an appropriate promoter, a transcription termination signal, and a selection marker gene (drug resistance gene, gene that complements auxotrophic mutation etc.). Also, it may contain a sequence encoding a tag sequence useful for separation and purification of the expressed protein and the like. Alternatively, the vector may be incorporated into the genome of a target host cell. The vector can be introduced into a target host cell by a transformation method known per se such as a competent cell method, a protoplast method, a calcium phosphate coprecipitation method and the like.

The above-mentioned "host cell" may be any cell as long as it can express a vector containing a nucleic acid encoding the above-mentioned CLA-ER, and bacterium, yeast, fungi, higher eukaryotic cell and the like can be mentioned. Examples of the bacterium include gram-positive bacteria such as *bacillus*, *Streptomyces* and the like and gram negative bacteria such as *Escherichia coli* and the like. A recombinant cell introduced with a vector containing a nucleic acid encoding CLA-ER can be cultivated by a method known per se which is suitable for the host cell.

"Purification" of the above-mentioned CLA-ER can be performed by a method known per se, for example, fungi collected by centrifugation and the like are ruptured by ultrasonication or glass beads and the like, solid such as cell debris is removed by centrifugation and the like, and the like to give a crude enzyme solution, which is subjected to a salting out method using ammonium sulfate, sodium sulfate and the like, chromatographys such as ion exchange chromatography, gel filtration chromatography, affinity chromatography and the like, gel electrophoresis and the like.

The amount of saturase to be added is, for example, 0.001-10 mg/ml, preferably 0.1-5 mg/ml, more preferably 0.2-2 mg/ml.

A "cofactor" may be used for reaction 4 and, for example, NADH and the like can be used. The concentration of addition may be any as long as the oxidation reaction proceeds efficiently. It is preferably 0.001-20 mM, more preferably 0.01-10 mM.

Furthermore, an "activator" may be used for the enzyme reaction and, for example, compounds similar to those recited as examples in the above-mentioned reaction 1 can be used at a similar addition concentration.

(Reaction 5)

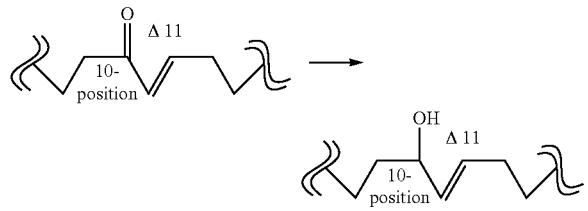

(Reaction 6)

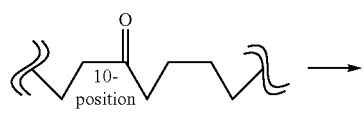

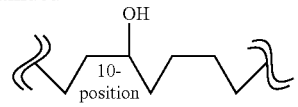

10-Hydroxy,trans-11 fatty acid is produced from an oxo fatty acid having 18 carbon atoms, a carbonyl group at the 10-position and a trans double bond at the 11-position (10-oxo,trans-11 fatty acid) by a dehydrogenase reaction (reaction 5) or 10-hydroxy,11,12-saturated fatty acid is produced from an oxo fatty acid having 18 carbon atoms and a carbonyl group at the 10-position and not having a double bond at the 11- and 12-positions (10-oxo,11,12-saturated fatty acid) by a dehydrogenase reaction (reaction 6).

The "substrate" of reaction 5 is not particularly limited as long as it is 10-oxo,trans-11 fatty acid produced by the above-mentioned reaction 3. Examples thereof include KetoC induced from KetoA, αKetoC induced from αKetoA, γKetoC induced from γKetoA, sKetoC induced from sKetoA and the like. The substrate may be obtained by a method other than reaction 3.

On the other hand, the "substrate" of reaction 6 is not particularly limited as long as it is 10-oxo,11,12-saturated fatty acid produced by the above-mentioned reaction 4. Examples thereof include KetoB induced from KetoC, αKetoB induced from αKetoC, γKetoB induced from γKetoC, sKetoB induced from sKetoC and the like. The substrate may be obtained by a method other than reaction 4.

While the dehydrogenase that catalyzes reaction 5 or reaction 6 is not particularly limited as long as it is an enzyme capable of utilizing 10-oxo,trans-11 fatty acid or 10-oxo,11,12-saturated fatty acid as a substrate and capable of converting to 10-hydroxy,trans-11 fatty acid or 10-hydroxy,11,12-saturated fatty acid, for example, *lactobacillus*-derived hydroxylated fatty acid-dehydrogenase (CLA-DH) is preferable. More preferred is *Lactobacillus plantarum*-derived CLA-DH, and particularly preferred is *L. plantarum* FERM BP-10549 strain-derived CLA-DH. While CLA-DH catalyzes the oxidation reaction in the above-mentioned reaction 2, it can also catalyze the reduction reaction in reaction 5 or reaction 6 as a reverse reaction.

The amount of dehydrogenase to be added is, for example, 0.001-10 mg/ml, preferably 0.1-5 mg/ml, more preferably 0.2-2 mg/ml.

A "cofactor" may be used for reaction 5 and reaction 6 and, for example, NADH, NADPH, FADH$_2$ and the like can be used. The concentration of addition may be any as long as the reduction reaction proceeds efficiently. It is preferably 0.001-20 mM, more preferably 0.01-10 mM.

Furthermore, an "activator" may be used for the enzyme reaction and, for example, compounds similar to those recited as examples in the above-mentioned reaction 1 can be used at a similar addition concentration.

In the above-mentioned each reaction, the enzymes (hydratase, dehydrogenase, isomerase, saturating enzyme) are subjected to the reaction system in the form of recombinant cells (e.g., *Escherichia coli, Bacillus subtilis*, yeast, insect cell, animal cell etc.) introduced with an expression vector containing a nucleic acid encoding same. In this case, the reaction can also be performed by cultivating the cells in a liquid medium suitable for the culture of the cells and added with a substrate and, where necessary, a cofactor and an activator. In addition, any of the above-mentioned enzymes may be a purified one or a crudely purified one. Alternatively, hydratase may be expressed in fungus such as *Escherichia coli* and the like and the fungus itself may be used or culture medium thereof may be used. Furthermore, the enzyme may be of a free type, or immobilized by various carriers.

The intestinal tract-protecting agent comprising hydroxylated fatty acid of the present invention can be applied to damage of intestinal tract barrier function or diseases caused thereby. Examples of the disease caused by damage of intestinal tract barrier function include, but are not limited to, inflammatory bowel diseases (Crohn's disease, ulcerative colitis as representative examples), ulcer, and pathology of irritable bowel syndrome.

Examples of the cause of damage of intestinal tract barrier function include, but are not limited to, stress, surgical causes such as operation and the like, drug, toxin and the like.

The intestinal tract-protecting agent of the present invention can be used for the prophylaxis or treatment of diseases caused by damage of intestinal tract barrier function in human, or warm-blooded animals other than human (e.g., dog, cat, mouse, rat, hamster, guinea pig, rabbit, swine, bovine, chicken, parakeet, hill myna, goat, horse, sheep, monkey etc.) by administering the agent to them.

An intestinal tract-protecting agent containing the hydroxylated fatty acid of the present invention can be used as, for example, a pharmaceutical product, a food, a feed and the like, or by adding the agent to them.

The dosage form of the pharmaceutical product includes dispersion, granule, pill, soft capsule, hard capsules, tablet, chewable tablet, quick-integrating tablet, syrup, liquid, suspension, suppository, ointment, cream, gel, adhesive, inhalant, injection and the like. A preparation thereof is prepared according to a conventional method. Since hydroxylated fatty acid and the like are poorly soluble in water, they are dissolved in a non-hydrophilic organic solvent such as plant-derived oil, animal-derived oil and the like or dispersed or emulsified in an aqueous solution together with an emulsifier, a dispersing agent, a surfactant and the like by a homogenizer (high-pressure homogenizer) and used.

Examples of the additives that can be used for formulating include animal and plant oils such as soybean oil, safflower oil, olive oil, germ oil, sunflower oil, beef fat, sardine oil and the like, polyalcohols such as polyethylene glycol, propylene glycol, glycerol, sorbitol and the like, surfactants such as sorbitan ester of fatty acid, sucrose ester of fatty acid, glycerin fatty acid ester, polyglycerol ester of fatty acid and the like, excipients such as purified water, lactose, starch, crystalline cellulose, D-mannitol, lecithin, gum arabic, sorbitol solution, carbohydrate solution and the like, sweetener, colorant, pH adjuster, flavor, various amino acids and the like. A liquid preparation may be dissolved or suspended in water or other suitable medium when in use. Also, tablet and granules may be coated by a well-known method.

For administration in the form of an injection, intravenous, intraperitoneal, intramuscular, subcutaneous, transdermal, intraarticular, intrasynovial, intrathecal, intraperiosteum, sublingual, oral administrations and the like are preferable, and intravenous administration or intraperitoneal administration is particularly preferable. The intravenous administration may be any of drip administration and bolus administration.

When the intestinal tract-protecting agent of the present invention is used as a food or a food additive, the form of the food is not particularly limited as long as it permits oral ingestion, such as solution, suspension, powder, solid formed article and the like. Specific examples include supplements (powder, granule, soft capsule, hard capsule, tablet, chewable tablet, quick-integrating tablet, syrup, liquid etc.), drinks (carbonic acid drinks, lactic acid drinks, sport drinks, fruit juice drinks, vegetable drinks, soymilk beverage, coffee drinks, tea drinks, powder drinks, concentrated drinks, nutrition drinks, alcohol drinks etc.), confectionery (gummy candy, jelly, gum, chocolate, cookie, candy, caramel, Japanese confectionery, snack etc.), instant food (instant noodles, retort food, can, microwavable foods, instant soup, miso soups, freeze-dried food etc.), oil, fats and oils food (mayonnaise, dressing, butter, cream, margarine etc.), wheat powder products (bread, pasta, noodle, cake mix, bread crumb etc.), seasoning (sauce, tomato processing seasoning, flavor seasoning, cooking mixture, soup etc.), processed meat products (meat ham, sausage etc.).

The above-mentioned foods can contain, where necessary, various nutrients, various vitamins (vitamin A, vitamin B1, vitamin B2, vitamin B6, vitamin C, vitamin D, vitamin E, vitamin K etc.), various minerals (magnesium, zinc, iron, sodium, potassium, selenium etc.), dietary fiber, dispersing agent, stabilizer such as emulsifier and the like, sweetener, flavor components (citric acid, malic acid etc.), flavor, royal jelly, propolis, *Agaricus* and the like.

When the intestinal tract-protecting agent of the present invention is used as a feed or a feed additive, the feed is, for example, pet food, stock raising or aquaculture feed additive and the like.

Only one kind of the hydroxylated fatty acid of the present invention may be blended with the pharmaceutical product, food, feed and the like of the present invention or two or more kinds thereof may be used in combination.

The dose of the pharmaceutical product of the present invention or the ingestion amount of the food of the present invention can be appropriately determined according to the age and body weight of the patients or those who ingest same, symptom, administration time, dosage form, administration method, combination of medicaments and the like. For example, when the pharmaceutical product of the present invention is orally administered, the total amount of the hydroxylated fatty acid of the present invention as an active ingredient is 0.02-100 mg/kg body weight, preferably 0.2-50 mg/kg body weight, per day for an adult, or 0.002 mg-50 mg/kg body weight, preferably 0.02-50 mg/kg body weight, by parenteral administration, which can be administered once a day or in several (2-5) portions per day. When it is ingested as a food, it can be added to a food such that the total ingestion amount of the hydroxylated fatty acid of the present invention as an active ingredient is 1-6000 mg, preferably 10-3000 mg, per day for an adult. The ingestion amount of the feed of the present invention can each appropriately determined according to the above-mentioned ingestion amount of the food and the above-mentioned dose of the pharmaceutical product.

The present invention is explained in more detail in the following by referring to Examples. The Examples are mere exemplifications of the present invention and do not limit the scope of the present invention in any manner.

EXAMPLES

Cell and Reagent

Caco-2 cells: ATCC accession No. HTB-37, after 40-60 passages, was used.
medium: Dulbecco's modified Eagle medium containing 10% fetal bovine serum, 1% non-essential amino acid, 100

IU/mL penicillin, 100 µg/mL streptomycin, and 50 µg/mL gentamicin (both medium and additives manufactured by Life Technologies)

Preparation of Caco-2 Cell

Caco-2 cells were placed in a 75 cm$^2$ tissue culture flask, and cultured up to about 80% confluence at 37° C. The cells were inoculated in a 12-well transwell (Transwell (registered trade mark)) cell culture chamber (permeable membrane; diameter 12 mm, pore size 0.4 µm) at a cell concentration of 2×10$^5$ cells/cm$^2$, and cultured at 37° C. for 14 days under 5% CO$_2$ atmosphere to give Caco-2 monolayer cells. Furthermore, to verify whether or not tight junction is sufficiently formed, Caco-2 monolayer cells having transepithelial electrical resistance (TER) of about 900-1,000 Ωcm$^2$ or more were used for the assay. Each well was set on a cluster plate, and filled with an outer side culture medium (basal side, 1.5 mL) and an inner side culture medium (luminal side, 0.5 mL). The medium was exchanged with a fresh medium every 48 hrs and Caco-2 monolayer cells were cultured.

Addition of Stimulation Agent and Test Fatty Acid Solution

To the inner side culture medium of each well of the Caco-2 monolayer cells prepared by the aforementioned method was added a solution of HYA, HYB, KetoA, KetoB or KetoC (each 50 µM concentration, 500 µL), and the mixture was cultured for 24 hr. Then, IFN-γ was added to the outer side culture medium to the final concentration of 50 ng/mL and, after culture for 24 hr, the outer side medium was once removed. TNF-α was added to 50 ng/mL, the mixture was further cultured for 6 hr, and the below-mentioned intestinal tract barrier protection effect was evaluated. Also, a well free of test fatty acid and added with IFN-γ and TNF-α, and a well free of test fatty acid solution, IFN-γ and TNF-α (hereinafter to be also referred to as control) were prepared.

Example 1

Comparison of Intestinal Tract Barrier Protection Effect

The intestinal tract barrier protection effect by test fatty acid solution was compared using transepithelial electrical resistance (TER) value (Ω·cm$^2$) and IL-8 production (pg/mL) as indices. With a resistance value measurement system (Millicell-ERS, Millipore) using an Ag/AgCl electrode, each TER value at 0, 1, 2, 3, 4, 5 and 6 hr after addition of TNF-α was measured. Furthermore, TER relative value (Relative TER) was calculated by dividing the TER value of each well by that of control. As for each IL-8 production amount, the outer side culture medium collected after culture was subjected to the ELISA method, and the value was measured 6 hr after TNF-α addition.

Figure 2:
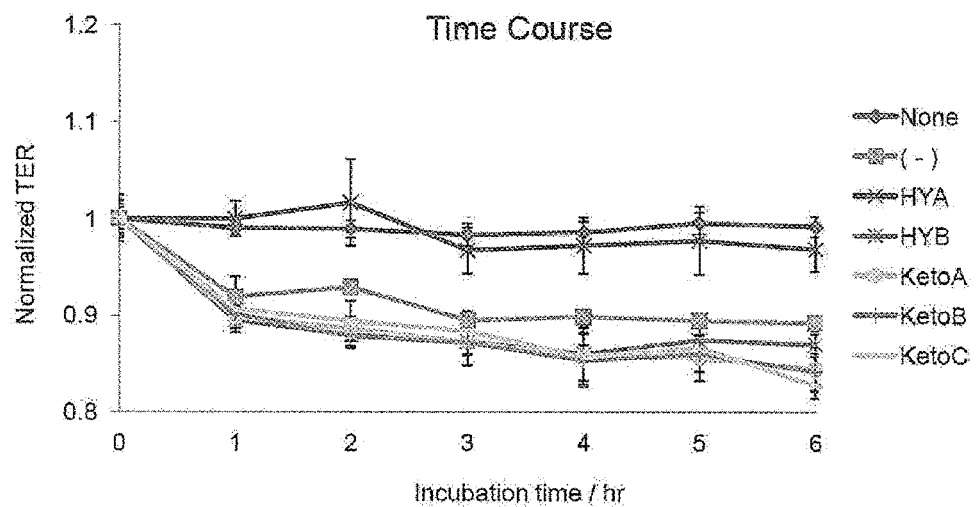
FIG. 2 shows the results of the intestinal tract barrier protection effect of the test fatty acids HYA, HYB, KetoA, KetoB and KetoC, by using transepithelial electrical resistance (hereinafter to be referred to as TER) of human colorectal cancer-derived cell line Caco-2 as an index. The vertical axis of FIG. 2A shows TER value ($\Omega$ cm$^2$), and the horizontal axis shows culture time. A well without addition of test fatty acid, IFN-$\gamma$ and TNF-$\alpha$ (indicated as None in Fig.), and a well without addition of test fatty acid and added with IFN-$\gamma$ and TNF-$\alpha$ (indicated as (-) in Fig.) were used as a control (hereinafter the same also in FIGS. 3-8 and 10).
Figure 2:
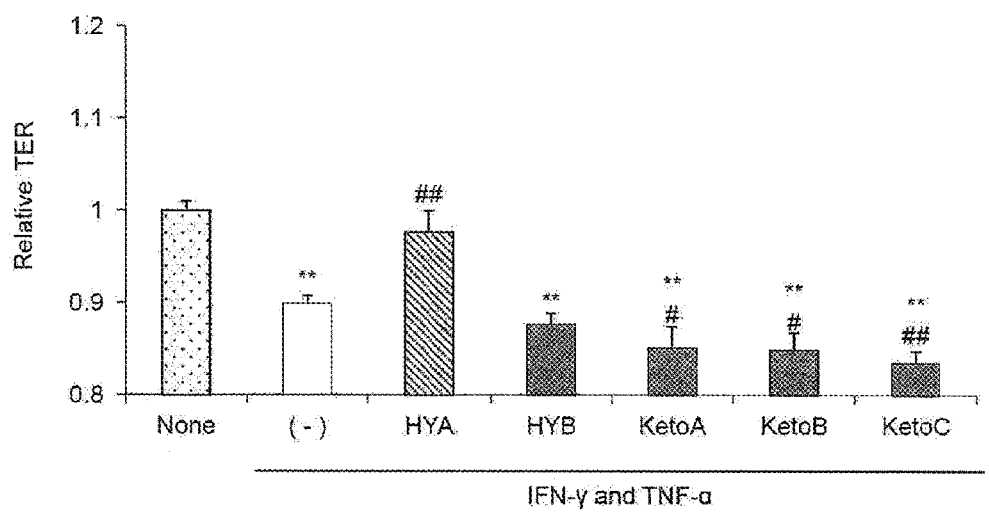
Figure 3:
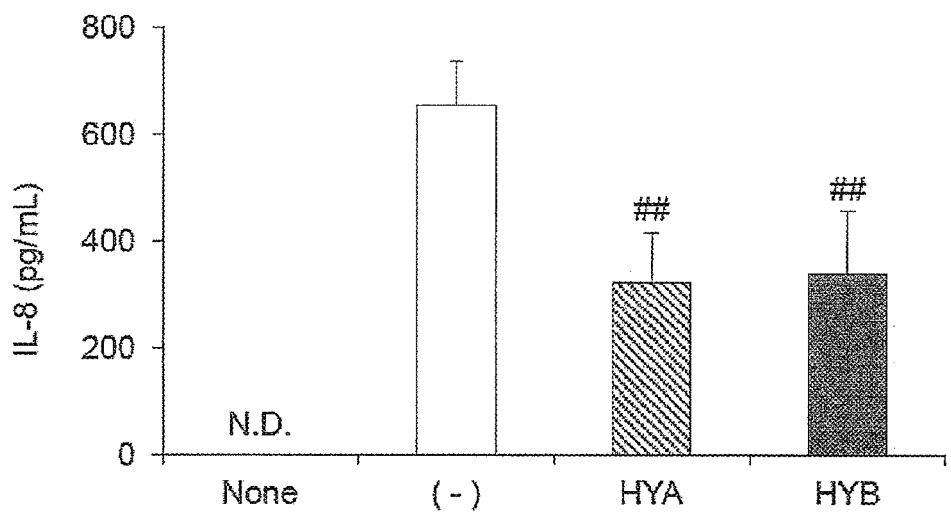
FIG. 3 shows the results of the intestinal tract barrier protection effects of HYA and HYB, examined using. IL-8 production in Caco-2 cells (both protein and gene levels were measured) as an index. The vertical axis of FIG. 3A shows IL-8 production amount (pg/mL). The vertical axis of FIG. 3B shows expression of IL-8 mRNA.
Figure 3:
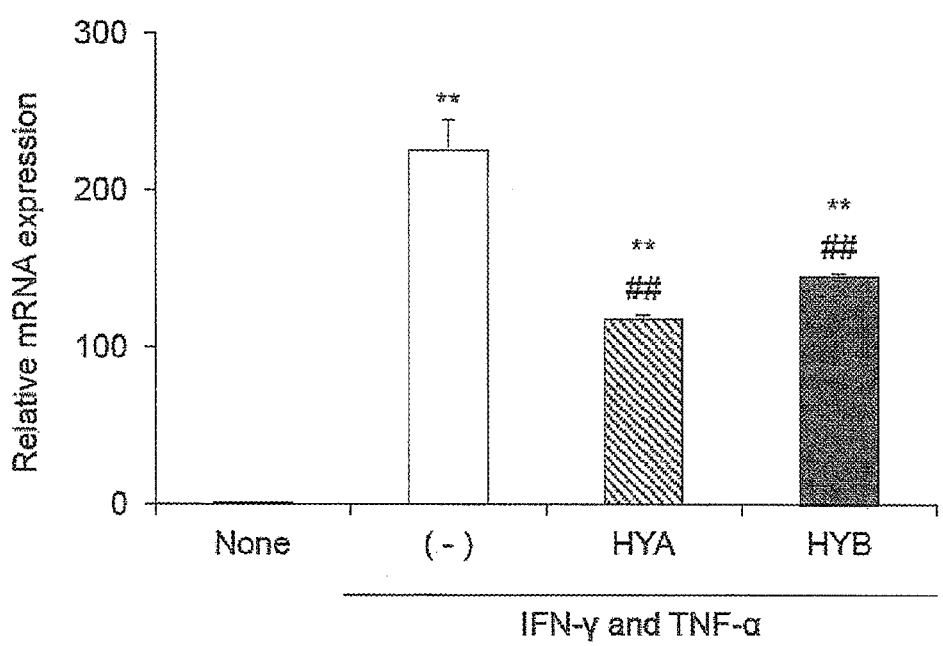

The measurement results of the TER relative value are shown in FIGS. 2A and B. The Figures show average±standard error (SE) (same in the following measurement results). Addition of IFN-γ and TNF-α to the Caco-2 monolayer cell culture system decreased the TER relative value. When a test fatty acid solution was added, only HYA showed suppression of a decrease in the TER relative value. The measurement results of IL-8 are shown in FIG. 3A. Addition of IFN-γ and TNF-α to the Caco-2a monolayer cell culture system increased concentration of IL-8 in the culture medium. When HYA and HYB were added, suppression of IL-8 production was observed.

Example 2

Effect of HYA on Gene Expression of Tight Junction-Related Factor

In the same manner as in the aforementioned Example, HYA was added and, 6 hr later, the Caco-2 monolayer cells were washed 3 times with PBS, and RNA was extracted with TRIzol (registered trade mark) (manufactured by Life Technologies) from the cells. RNA was reverse-transcribed using a high-capacity cDNA reverse transcription kit (Life Technologies) to give cDNA, and real-time PCR analysis was performed using KAPA SYBR FAST ABI PRISM qPCR kit (Kapa Biosystems). As the primer, oligoDNA pairs of nucleotide sequences were used: SEQ ID NOs: 3 and 4 for IL-8, SEQ ID NOs: 5 and 6 for Claudin-1, SEQ ID NOs: 7 and 8 for ZO-1, SEQ ID NOs: 9 and 10 for Occludin, and SEQ ID NOs: 11 and 12 for MLCK.

Figure 4:
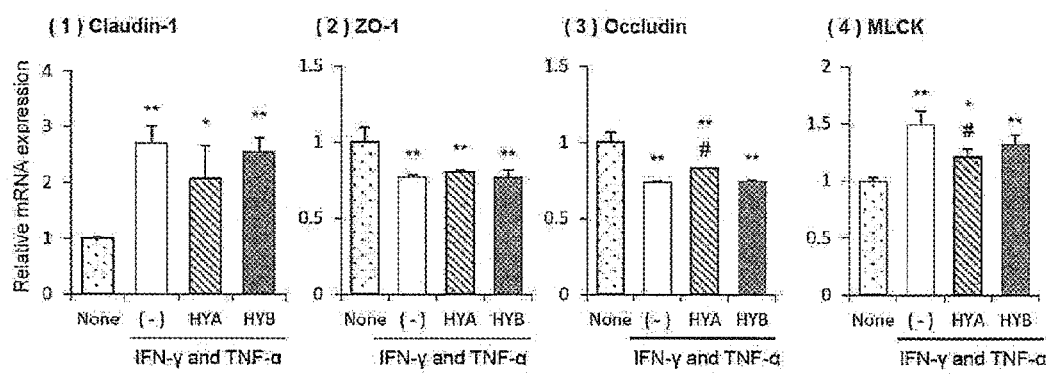
FIG. 4 shows the effects of HYA and HYB on the gene expression of tight junction-related factors.
Figure 4:
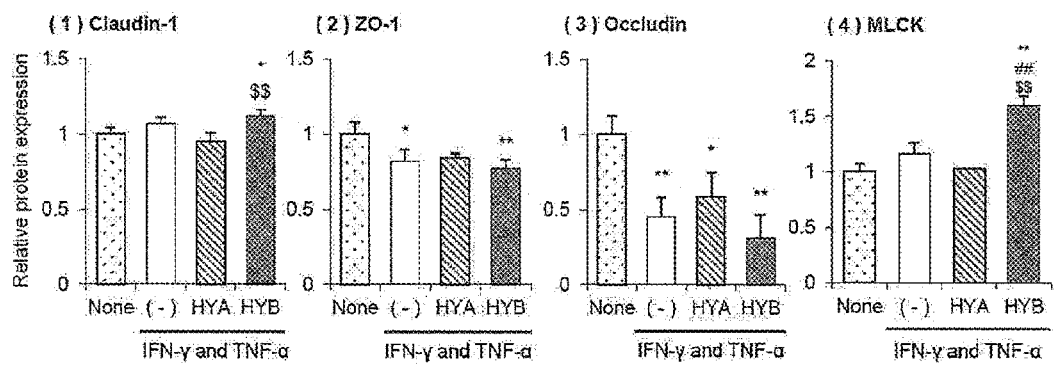

The results of gene expression analysis are shown in FIG. 4. Addition of IFN-γ and TNF-α to Caco-2 monolayer cell culture system increased mRNA expression of myosin light chain kinase (MLCK), and decreased mRNA expression of occludin. The cells added with HYA showed suppression of an increase in the mRNA expression of MLCK and a decrease in the mRNA expression of occludin. As shown in FIG. 3B, addition of IFN-γ and TNF-α increased the mRNA expression of IL-8; however, addition of HYA and HYB suppressed such increase in the expression.

Example 3

Effect of HYA on Dextran Sodium Sulfate-Induced Enteritis Model Mouse

BALB/c mice (♀, 6-week-old) were purchased from Charles River Japan (Kanagawa, Japan), and all experiment plans were carried out in accordance with Hiroshima University, Animal Experiment Rule (No. C10-17). Acute colitis was induced by allowing free intake of 3.5% (w/v) DSS (molecular weight 36000-50000; MP Biomedicals, Aurora, Ohio, USA) for 5 days. To evaluate the effect of HYA and HYB on large intestine, 100 µL of a suspension of HYA or HYB (each 100 nmol) was orally administered to the mice. This administration was performed every day for total 10 days, for 5 days before DSS administration and 5 days after the start of the administration. The symptoms of colitis were evaluated every day based on a decrease in body weight, condition of feces and bleeding from the anus. After administration of DSS for 5 days, the mouse was sacrificed, and the length of the large intestine was measured. Thereafter, RNA was extracted from the large intestine tissue by using RNeasy Mini Kit (Qiagen, Maryland, Md., USA). Paraffin section (7 µm) of the large intestine tissue was produced, stained with hematoxylin-eosin, and histochemically evaluated. The extracted RNA was reverse-transcribed using a high-capacity cDNA reverse transcription kit (Life Technologies) to give cDNA, and real-time PCR analysis was performed using a KAPA SYBR FAST ABI PRISM qPCR kit (Kapa Biosystems). As the primer, oligoDNA pairs of nucleotide sequences were used: SEQ ID NOs: 5 and 6 for Claudin-1, SEQ ID NOs: 13 and 14 for Claudin-3, SEQ ID NOs: 15 and 16 for Claudin-4, SEQ ID NOs: 7 and 8 for ZO-1, SEQ ID NOs: 17 and 18 for ZO-2, SEQ ID NOs: 9 and 10 for Occludin, and SEQ ID NOs: 11 and 12 for MLCK.

Figure 5:
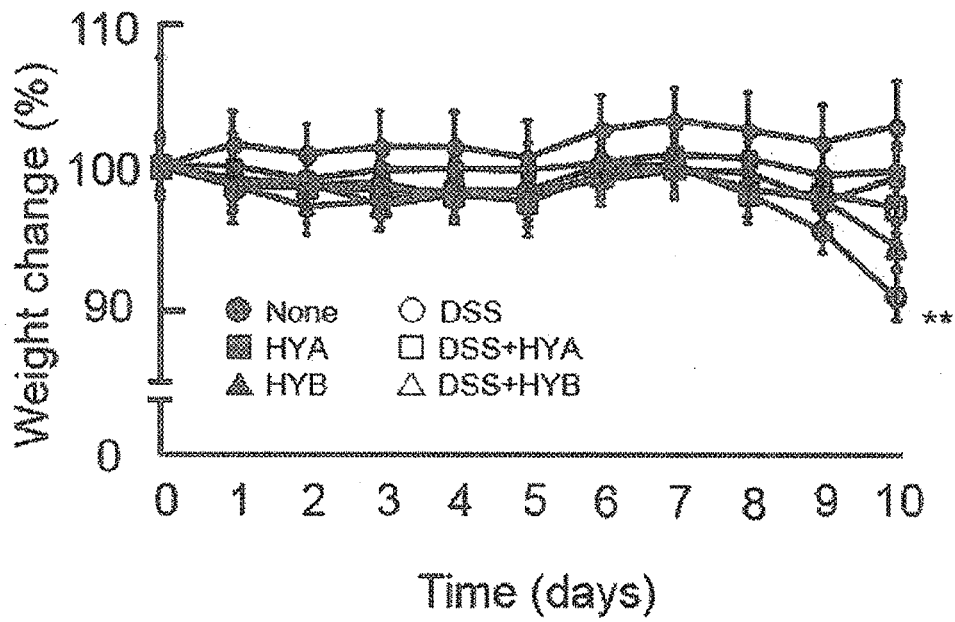
FIG. 5 shows the effect of HYA or HYB administration on time-course changes in the body weight of DSS-induced enteritis model mouse (% change relative to body weight at the start of HYA or HYB administration as 100%).
Figure 6:
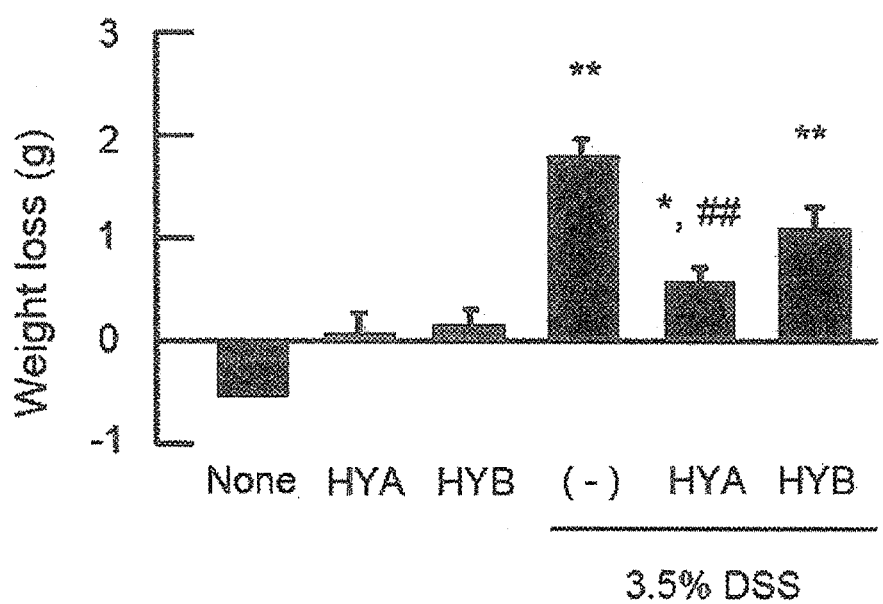
FIG. 6 shows the effect of HYA or HYB administration on a decrease in the body weight of DSS-induced enteritis model mouse (amount of decrease (g) from start of HYA or HYB administration to end of DSS 5 day administration).
Figure 7:
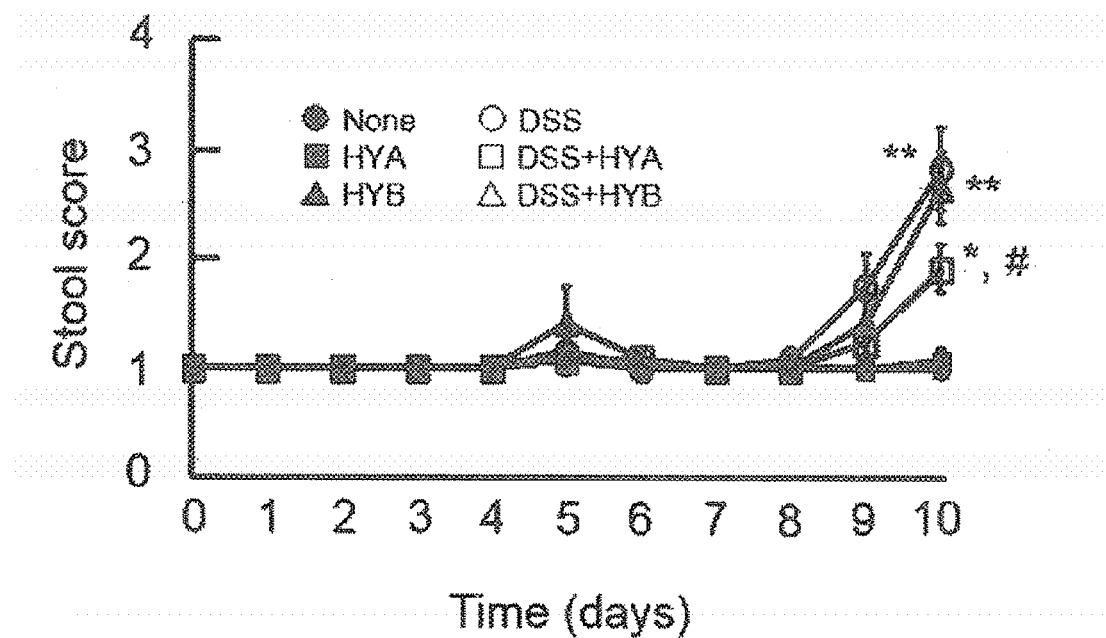
FIG. 7 shows the effect of HYA or HYB administration on time-course changes in the feces score of DSS-induced enteritis model mouse.
Figure 8:
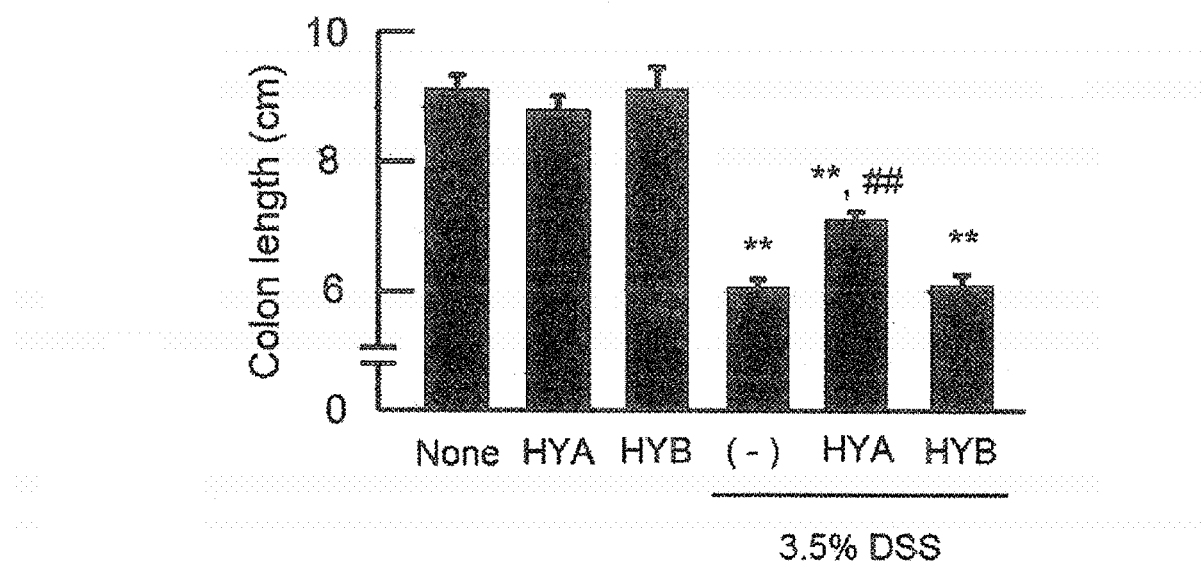
FIG. 8 shows the effect of HYA or HYB administration on the length of large intestine of DSS-induced enteritis model mouse.

As for the mice in each treatment group, time-course changes in the body weight are shown in FIG. 5, weight loss is shown in FIG. 6, stool score is shown in FIG. 7, and the length of large intestine is shown in FIG. 8. Administration of HYA was effective for the suppression of weight loss, recovery of stool score and protection of large intestine.

Figure 9:
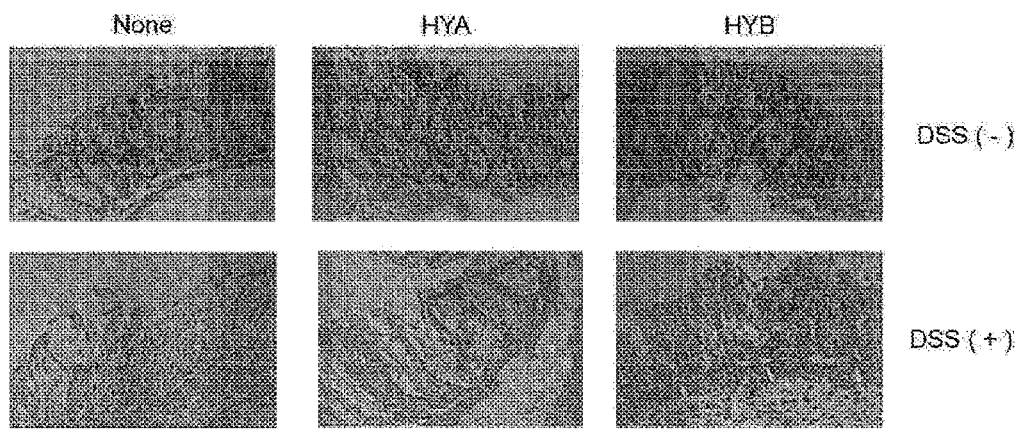
FIG. 9 shows the effect of HYA or HYB administration on epithelial cell damage of the large intestine of DSS-induced enteritis model mouse.
Figure 10:
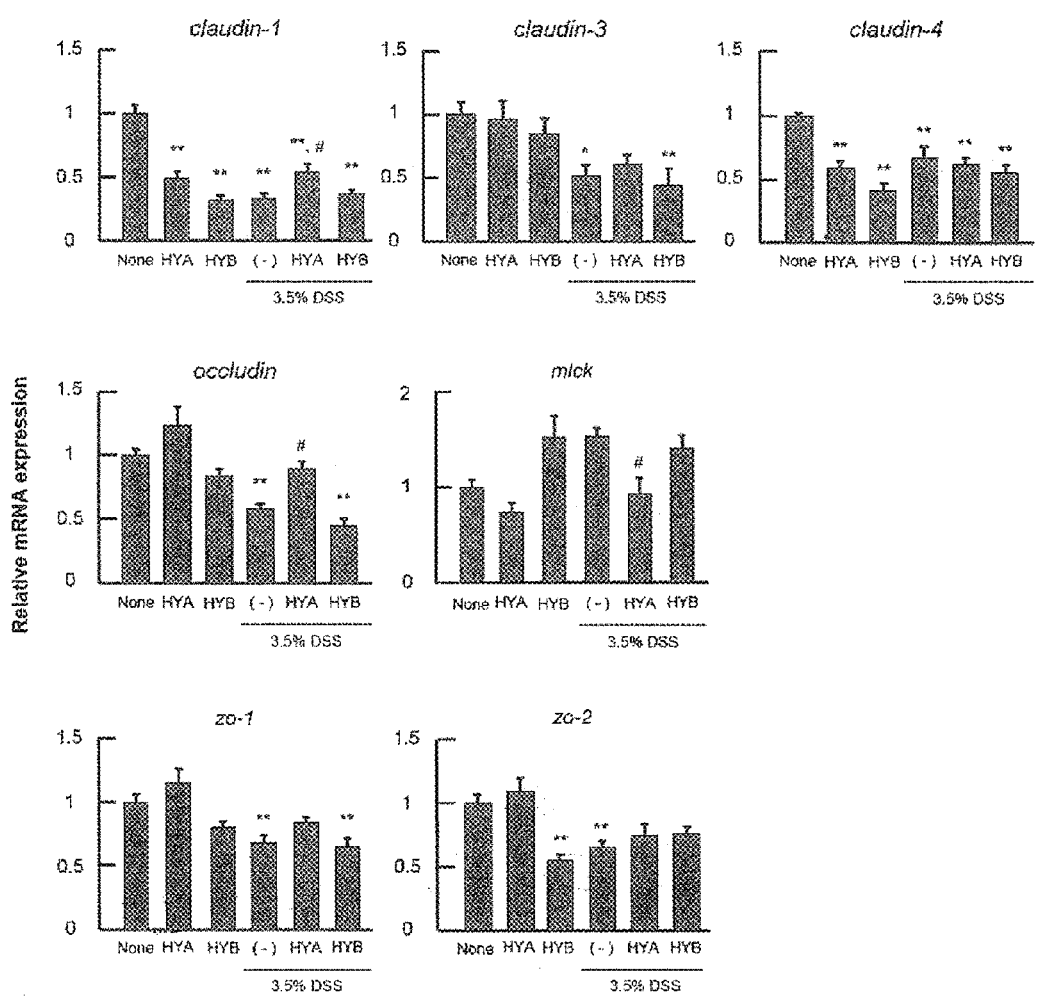
FIG. 10 shows the effect of HYA and HYB on the gene expression of tight junction-related factors in large intestinal tissues of DSS-induced enteritis model mouse.

The results of the histochemical evaluation of the large intestine section (H&E staining) are shown in FIG. 9. While the DSS treatment remarkably induced damage of epithelial cells of the large intestine and decrease of crypt, the mouse administered with HYA showed recovery of tissue damage.

mRNA expression of claudin-1, -3, and -4, occludin, MLCK, ZO-1 and ZO-2 is shown in FIG. 10. DSS mouse significantly induced abnormal mRNA expression of claudin-1, 3, 4, occludin, ZO-1 and ZO-2 (MLCK tended to increase). However, the mice orally administered with HYA showed significant recovery of the mRNA expression of occludin and MLCK as compared to the DSS mouse. On the other hand, HYB did not show recovery from abnormal expression of all TJ-associated factors.

INDUSTRIAL APPLICABILITY

The present invention has clarified that hydroxylated fatty acid, particularly unsaturated hydroxylated fatty acid, has a conventionally-unknown intestinal tract barrier effect as a physiological function. An intestinal tract-protecting agent containing such hydroxylated fatty acid and the like is applicable to various fields of pharmaceutical products, foods, feed and the like, and the present invention is industrially extremely useful.

While the present invention has been described with emphasis on preferred embodiments, it is obvious to those skilled in the art that the preferred embodiments can be modified.

The contents disclosed in any publication cited herein, including patents and patent applications, are hereby incorporated in their entireties by reference, to the extent that they have been disclosed herein.

This application is based on a patent application No. 2013-031769 filed in Japan on Feb. 21, 2013, the contents of which are incorporated in full herein by reference.

The invention claimed is:

1. A method for the prophylaxis or treatment of damage in intestinal tract barrier function or a disease caused by the damage in a mammal, comprising administering an effective amount of a hydroxylated fatty acid having 18 carbon atoms and having a hydroxyl group at the 10-position to the mammal, thereby treating or preventing damage in intestinal tract barrier function or a disease caused by the damage.

2. The method according to claim 1, wherein the disease caused by damage in intestinal tract barrier function is at least one kind of disease selected from the group consisting of inflammatory bowel disease, ulcer and irritable bowel syndrome.

3. The method according to claim 1, wherein the hydroxylated fatty acid is a hydroxylated unsaturated fatty acid.

4. The method according to claim 3, wherein the disease caused by damage in intestinal tract barrier function is at least one kind of disease selected from the group consisting of inflammatory bowel disease, ulcer and irritable bowel syndrome.

5. The method according to claim 3, wherein the hydroxylated unsaturated fatty acid has a cis double bond at the 12-position.

6. The method according to claim 5, wherein the disease caused by damage in intestinal tract barrier function is at least one kind of disease selected from the group consisting of inflammatory bowel disease, ulcer and irritable bowel syndrome.

7. The method according to claim 3, wherein the hydroxylated unsaturated fatty acid is 10-hydroxy-cis-12-octadecenoic acid.

8. The method according to claim 7, wherein the disease caused by damage in intestinal tract barrier function is at least one kind of disease selected from the group consisting of inflammatory bowel disease, ulcer and irritable bowel syndrome.

* * * * *

SEQUENCE LISTING

```
<160> NUMBER OF SEQ ID NOS: 18

<210> SEQ ID NO 1
<211> LENGTH: 654
<212> TYPE: DNA
<213> ORGANISM: Lactobacillus plantarum
<220> FEATURE:
<221> NAME/KEY: CDS
<222> LOCATION: (1)..(654)

<400> SEQUENCE: 1 atg tca gaa gca gtg aaa aat ttg gtg aac aat gat tta gca gac gtg      48
Met Ser Glu Ala Val Lys Asn Leu Val Asn Asn Asp Leu Ala Asp Val
1               5                   10                  15 atg ttt aac cgc cat tca gtt cgg cag ttt gac ccg aac gtt aaa att      96
Met Phe Asn Arg His Ser Val Arg Gln Phe Asp Pro Asn Val Lys Ile
            20                  25                  30 gga cgt gat gag tta caa aag atg att gcg gaa gca gcc acc gcg cca     144
Gly Arg Asp Glu Leu Gln Lys Met Ile Ala Glu Ala Ala Thr Ala Pro
        35                  40                  45 tcg gca tgt aat tta cag tca tgg cac ttt gtc gtc gtg gat acc ccc     192
Ser Ala Cys Asn Leu Gln Ser Trp His Phe Val Val Val Asp Thr Pro
    50                  55                  60 gag gca aag gct aag ttc aaa caa gcc gtg atg aaa ttc aac tac cca     240
Glu Ala Lys Ala Lys Phe Lys Gln Ala Val Met Lys Phe Asn Tyr Pro
65                  70                  75                  80 cag gtc gac agt gca tcg gcc atc gtc ttt att gcc ggt gac acc cag     288
Gln Val Asp Ser Ala Ser Ala Ile Val Phe Ile Ala Gly Asp Thr Gln
                85                  90                  95 tcg cat tat gtt tat cgc gat gtc tgg aac aaa gtt tat gag gat ggg     336
Ser His Tyr Val Tyr Arg Asp Val Trp Asn Lys Val Tyr Glu Asp Gly
            100                 105                 110 aat att acg aag gaa cgc ttg gat cag att ctg gga acc ttc tta cca     384
Asn Ile Thr Lys Glu Arg Leu Asp Gln Ile Leu Gly Thr Phe Leu Pro
        115                 120                 125 tta tat gaa aat gcc aca cca gat ttc ttg aaa ttc gat gcg acg att     432
Leu Tyr Glu Asn Ala Thr Pro Asp Phe Leu Lys Phe Asp Ala Thr Ile
    130                 135                 140 gat tgt tcc gtt gtc ggg atg cag ttg ctg cta gtg gca cgg gct cat     480
Asp Cys Ser Val Val Gly Met Gln Leu Leu Leu Val Ala Arg Ala His
```

```
ggg tat gat gcc aat gcg ttc tcc gga att gac ttt gaa aag atg att    528
Gly Tyr Asp Ala Asn Ala Phe Ser Gly Ile Asp Phe Glu Lys Met Ile
            165                 170                 175 ccg acg ctg ggt ctt gat cct aaa cga tac gtg cca gta atg ggg atc    576
Pro Thr Leu Gly Leu Asp Pro Lys Arg Tyr Val Pro Val Met Gly Ile
        180                 185                 190 gca atc ggg aaa gca gcg caa gaa ccg ctc cat acg act cgg tac gat    624
Ala Ile Gly Lys Ala Ala Gln Glu Pro Leu His Thr Thr Arg Tyr Asp
    195                 200                 205 gcc aaa aca cag act gat ttc tta gcc taa                            654
Ala Lys Thr Gln Thr Asp Phe Leu Ala
    210                 215
```

<210> SEQ ID NO 2
<211> LENGTH: 217
<212> TYPE: PRT
<213> ORGANISM: Lactobacillus plantarum

<400> SEQUENCE: 2

```
Met Ser Glu Ala Val Lys Asn Leu Val Asn Asn Asp Leu Ala Asp Val
1               5                   10                  15

Met Phe Asn Arg His Ser Val Arg Gln Phe Asp Pro Asn Val Lys Ile
            20                  25                  30

Gly Arg Asp Glu Leu Gln Lys Met Ile Ala Glu Ala Ala Thr Ala Pro
        35                  40                  45

Ser Ala Cys Asn Leu Gln Ser Trp His Phe Val Val Asp Thr Pro
    50                  55                  60

Glu Ala Lys Ala Lys Phe Lys Gln Ala Val Met Lys Phe Asn Tyr Pro
65                  70                  75                  80

Gln Val Asp Ser Ala Ser Ala Ile Val Phe Ile Ala Gly Asp Thr Gln
                85                  90                  95

Ser His Tyr Val Tyr Arg Asp Val Trp Asn Lys Val Tyr Glu Asp Gly
            100                 105                 110

Asn Ile Thr Lys Glu Arg Leu Asp Gln Ile Leu Gly Thr Phe Leu Pro
        115                 120                 125

Leu Tyr Glu Asn Ala Thr Pro Asp Phe Leu Lys Phe Asp Ala Thr Ile
    130                 135                 140

Asp Cys Ser Val Val Gly Met Gln Leu Leu Leu Val Ala Arg Ala His
145                 150                 155                 160

Gly Tyr Asp Ala Asn Ala Phe Ser Gly Ile Asp Phe Glu Lys Met Ile
                165                 170                 175

Pro Thr Leu Gly Leu Asp Pro Lys Arg Tyr Val Pro Val Met Gly Ile
            180                 185                 190

Ala Ile Gly Lys Ala Ala Gln Glu Pro Leu His Thr Thr Arg Tyr Asp
        195                 200                 205

Ala Lys Thr Gln Thr Asp Phe Leu Ala
    210                 215
```

<210> SEQ ID NO 3
<211> LENGTH: 24
<212> TYPE: DNA
<213> ORGANISM: Artificial sequence
<220> FEATURE:
<223> OTHER INFORMATION: Primer

<400> SEQUENCE: 3
atgacttcca agctggccgt ggct                                         24

<210> SEQ ID NO 4
<211> LENGTH: 25
<212> TYPE: DNA
<213> ORGANISM: Artificial sequence
<220> FEATURE:
<223> OTHER INFORMATION: Primer

<400> SEQUENCE: 4
tctcagccct cttcaaaaac ttctc                                         25

<210> SEQ ID NO 5
<211> LENGTH: 20
<212> TYPE: DNA
<213> ORGANISM: Artificial sequence
<220> FEATURE:
<223> OTHER INFORMATION: Primer

<400> SEQUENCE: 5
ccctatgacc ccagtcaatg                                               20

<210> SEQ ID NO 6
<211> LENGTH: 20
<212> TYPE: DNA
<213> ORGANISM: Artificial sequence
<220> FEATURE:
<223> OTHER INFORMATION: Primer

<400> SEQUENCE: 6
aaggcagaga gaagcagcag                                               20

<210> SEQ ID NO 7
<211> LENGTH: 20
<212> TYPE: DNA
<213> ORGANISM: Artificial sequence
<220> FEATURE:
<223> OTHER INFORMATION: Primer

<400> SEQUENCE: 7
ggatgatgcc tcgttctacc                                               20

<210> SEQ ID NO 8
<211> LENGTH: 20
<212> TYPE: DNA
<213> ORGANISM: Artificial sequence
<220> FEATURE:
<223> OTHER INFORMATION: Primer

<400> SEQUENCE: 8
tccgtgttgt ggataccttg                                               20

<210> SEQ ID NO 9
<211> LENGTH: 25
<212> TYPE: DNA
<213> ORGANISM: Artificial sequence
<220> FEATURE:
<223> OTHER INFORMATION: Primer

<400> SEQUENCE: 9
aagagttgac agtcccatgg catac                                         25

<210> SEQ ID NO 10
<211> LENGTH: 24
<212> TYPE: DNA
<213> ORGANISM: Artificial sequence
<220> FEATURE:

```
<223> OTHER INFORMATION: Primer

<400> SEQUENCE: 10
atccacaggc gaagttaatg gaag                                          24

<210> SEQ ID NO 11
<211> LENGTH: 23
<212> TYPE: DNA
<213> ORGANISM: Artificial sequence
<220> FEATURE:
<223> OTHER INFORMATION: Primer

<400> SEQUENCE: 11
aacgagatca acatcatgaa cca                                           23

<210> SEQ ID NO 12
<211> LENGTH: 20
<212> TYPE: DNA
<213> ORGANISM: Artificial sequence
<220> FEATURE:
<223> OTHER INFORMATION: Primer

<400> SEQUENCE: 12
cagctgtgct tgctctcgaa                                               20

<210> SEQ ID NO 13
<211> LENGTH: 20
<212> TYPE: DNA
<213> ORGANISM: Artificial sequence
<220> FEATURE:
<223> OTHER INFORMATION: Primer

<400> SEQUENCE: 13
aaggtgtacg actcgctgct                                               20

<210> SEQ ID NO 14
<211> LENGTH: 21
<212> TYPE: DNA
<213> ORGANISM: Artificial sequence
<220> FEATURE:
<223> OTHER INFORMATION: Primer

<400> SEQUENCE: 14
gaagtcccgg ataatggtgt t                                             21

<210> SEQ ID NO 15
<211> LENGTH: 20
<212> TYPE: DNA
<213> ORGANISM: Artificial sequence
<220> FEATURE:
<223> OTHER INFORMATION: Primer

<400> SEQUENCE: 15
tatggatgaa ctgcgtggtg                                               20

<210> SEQ ID NO 16
<211> LENGTH: 20
<212> TYPE: DNA
<213> ORGANISM: Artificial sequence
<220> FEATURE:
<223> OTHER INFORMATION: Primer

<400> SEQUENCE: 16
ccacgatgat gctgatgatg                                               20
```

```
<210> SEQ ID NO 17
<211> LENGTH: 20
<212> TYPE: DNA
<213> ORGANISM: Artificial sequence
<220> FEATURE:
<223> OTHER INFORMATION: Primer

<400> SEQUENCE: 17
aaagcagagc gaacgaagag                                                    20

<210> SEQ ID NO 18
<211> LENGTH: 20
<212> TYPE: DNA
<213> ORGANISM: Artificial sequence
<220> FEATURE:
<223> OTHER INFORMATION: Primer

<400> SEQUENCE: 18
tttagttgcc agacccgttc                                                    20
```